United States Patent [19]

Riano

[11] Patent Number: Plant 7,364

[45] Date of Patent: Oct. 23, 1990

[54] NECTARINE TREE "SUN BURST"

[76] Inventor: Cedric J. Riano, 9905 Avenue 404, Dinuba, Calif. 93618

[21] Appl. No.: 334,574

[22] Filed: Apr. 7, 1989

[51] Int. Cl.[5] ..... A01H 5/00

[52] U.S. Cl. ..... Plt./41

[58] Field of Search ..... Plt./41

*Primary Examiner*—James R. Feyrer

*Attorney, Agent, or Firm*—Worrel & Worrel

[57] ABSTRACT

A new and distinct variety of nectarine tree which is somewhat remotely similar to the Sun Grand Nectarine Tree (U.S. Plant Pat. No. 974) with which it is most closely related but from which it is distinguished therefrom by producing fruit which are mature for harvesting and shipment approximately five weeks following the fruit produced by the Sun Grand Nectarine Tree and which further produces globose shaped fruit which is clingstone by nature and which further exhibits a yellow and red skin color and a pleasing yellow-colored flesh.

1 Drawing Sheet

BACKGROUND OF THE NEW VARIETY

The present invention relates to a new and distinct variety of nectarine tree which will hereinafter be denominated varietally as "Sun Burst" and more particularly to a nectarine tree which produces fruit which are mature for commercial harvesting and shipment approximately August 10 through August 20 in the San Joaquin Valley of central California, and which further is distinguished principally as to novelty by producing a clingstone fruit, the flesh of which is very firm and crisp, and which has noteworthy shipping and handling characteristics.

The applicant has been engaged in farming operations throughout most of his professional career. In connection with these duties, the applicant, during routine orchard operations in 1984, discovered a newly found seedling of unknown parentage growing in an orchard of Sun Grand Nectarine Trees (U.S. Plant Pat. No. 974) on his ranch which is located on Road 104 between Avenues 404 and 408 near Sultana, Calif. The fruit produced by the newly found seedling were noted at that time to have a novel skin color and a harvesting date which appeared somewhat later than the trees growing in the immediate geographical vicinity. The applicant marked the newly found seedling for subsequent observation.

ORIGIN AND ASEXUAL REPRODUCTION OF THE NEW VARIETY

The present variety of nectarine tree hereof was discovered by the inventor in his orchard which is located near Road 104 and between Avenues 404 and 408 near Sultana, Calif. The applicant discovered the newly found seedling within the cultivatred area of an orchard of Sun Grand Nectarine Trees (U.S. Plant Pat. No. 974). The discovery, which occurred during routine orchard operations in the summer of 1984, was noted at that time to produce fruit which had a noteworthy skin color and a harvesting date which appeared somewhat later than the remainder of the fruit trees growing in the same vicinity. More particularly, the Sun Grand Nectarine Tree has long been known for its production of relatively large, firm, freestone fruit which ripen for commercial harvesting and shipment approximately July 5 in the San Joaquin Valley of Central California.

In contrast to the Sun Grand nectarine tree, the subject variety was noted as producing a clingstone fruit which had a firm yellow-colored flesh with a fair amount of red coloration spreading into the flesh some distance from the pit cavity. Further the new variety was noted for producing leaves which were significantly larger in dimension than those displayed on typically mature Sun Grand Nectarine Trees. After observing the subject tree for several months and evaluating the fruit produced thereby, the inventor in the winter of 1985, removed bud wood from the newly found seedling and grafted it into test trees which were located at 9905 Avenue 404 in Dinuba, Calif. This first asexual reproduction produced varying amounts of fruit in 1986, 1987 and 1988. It has subsequently been determined that this first asexual reproduction dependably and accurately reproduced the superior characteristics observed by the applicant in the original newly found seedling.

SUMMARY OF THE NEW VARIETY

The Sun Burst Nectarine Tree is characterized as to novelty by producing a clingstone fruit which has an appealing shape and a highly attractive skin color. Further the fruit produced by the Sun Burst Nectarine Tree is ripe for commercial harvesting and shipment approximately August 10 through August 20 in the San Joaquin Valley of Central California. The new and novel variety is most closely similar to the Sun Grand Nectarine Tree (U.S. Plant Pat. No. 974) from which it is believed it was derived as a newly found seedling, but which is distinguishable therefrom and characterized principally as to novelty by producing fruit which are ripe for harvesting and shipment approximately five weeks after the Sun Grand Nectarine Tree and which further produces a clingstone fruit having noteworthy shipping and handling characteristics.

BRIEF DESCRIPTION OF THE DRAWINGS

The drawing is a color photograph of several mature fruit characteristic of the subject variety. The several fruit shown in the photograph display the skin colorations typical of fruit which are sufficiently mature for commercial harvesting and shipment. Another cross-sectioned fruit is shown displaying the flesh coloration of a typically mature fruit. The drawing also shows a typical twig bearing characteristic leaves which display the top and bottom surface colors thereof together with a typical stone, all of the instant variety.

DETAILED DESCRIPTION

Referring more specifically to the pomological details of this new and distinct variety of nectarine tree, the following has been observed under the ecological conditions prevailing at the orchard of origin which is located in close proximity to Road 104 and between Avenues 404 and 408 near Sultana, Calif. All major color code designations are by reference to the Dictionary of Color, by Maerz and Paul, Second Edition, 1950 or alternatively by reference to the Inter-Society Color Council, National Bureau of Standards. Common color names are also employed occasionally.

TREE

GENERALLY:

*Size.*—Average as compared with other nectarine cultivars.

*Vigor.*—Very vigorous.

*Chilling requirements.*—Average as compared with other nectarine varieties growing in the San Joaquin Valley of Central California. Very hardy.

*Figure.*—Upright, to upright spreading, and vase formed. The final form of the tree will, however, be determined by pruning practices.

*Productivity.*—Noteworthy. The subject variety is considered to be heavily productive.

*Regularity of bearing.*—Regular. The subject variety has produced a good crop during the last several years it was observed.

TRUNK:

*Size.*—Average.

*Surface texture.*—Normal.

*Color.*—Gray-brown (7-E-9).

*Lenticels — numbers.*—Approximately 18 lenticels per square inch were observed.

*Lenticels — size.*—Average.

BRANCHES:

*Size.*—Average.

*Surface texture.*—Moderately rough.

*Color — One year or older wood.*—Brown, (6-A-9).

*Color — Immature branches.*—Green, (120 m. Y G).

*Surface texture — immature growth.*—Smooth.

*Lenticels — Numbers.*—Average.

*Lenticels — Size.*—Medium.

LEAVES

Size:

*Generally.*—Large as compared with other nectarine cultivars.

*Average length.*—Approximately 20.5 through 23 cm.

*Average width.*—Approximately 5.2 cm.

Form: Lanceolate with an acuminate tip, and having an acute base; the leaf tip may appear slightly twisted.

Color:

*Upwardly disposed surface.*—Green, (125. m. Ol G).

*Downwardly disposed surface.*—Pale green, (120. m. Y G).

*Leaf vein.*—The leaf vein color on the bottom surface of the leaf appears yellow-green (119. l. Y G).

Marginal form:

*Generally.*—Crenate and appearing at times moderately coarse, the crenations are regular.

*Leaf vein.*—Thickness — Approximately 1 mm. when measured at the approximate center of the leaf.

*Leaf margin.*—Undulate.

Glandular characteristics: Pinnately, net veined.

Petiole:

*Size.*—Average.

*Length.*—Approximately 14–16 mm.

*Thickness.*—Approximately 1.5 mm.

*Color.*—Yellow-green, (119. l. Y G). The color of the petiolar groove is somewhat darker (118. Deep Y G).

Stem glands:

*Form.*—Variable, appearing predominantly reniform although occasionally globose types may be evident.

*Position.*—One or two, and occasionally three stem glands may appear on the upper petiole; and one or two stem glands may appear on the basal portion of the leaf margin.

*Pattern.*—Alternate.

*Color.*—A light green-yellow color which is somewhat similar to the color of the leaf mid-vein (119. l. Y G).

Stipules: Not evident.

FLOWERS

Flower buds:

*Size.*—Average.

*Surface texture.*—Quite similar to the Sun Grand Nectarine Tree (U.S. Plant Pat. No. 974).

Flowers:

*Generally.*—The flowers of the subject variety are not particularly distinctive.

Date of bloom: During the last week of February and the first week of March in 1988. The date of bloom is quite similar to the date of bloom for the Sun Grand Nectarine Tree (U.S. Plant Pat. No. 974).

Size:

*Generally.*—Considered medium to large as compared with other nectarine cultivars.

Petals:

*Color.*—Light pink (250. m. p Pk.). Further, it was observed that the petals of the subject variety color from the stem portion outwardly.

FRUIT

Maturity when described: Ripe for commercial harvesting and shipment approximately August 10 through August 20 near Sultana, Calif.

Size:

*Generally.*—Variable, considered medium to large.

*Average diameter in the axial plane.*—Variable, approximately 64 mm.–75 mm.

*Average diameter transverse in the suture plane.*—Approximately 64 mm.–73 mm.

*Average diameter transverse and at right angles to the suture plane.*—Approximately 62 mm.–68 mm.

Form:

*Uniformity.*—Uniform.

*Symmetry.*—Asymmetrical, with one side appearing nearly always slightly larger than the other side. Ovate and occasionally oval in appearance in its lateral aspect and nearly globose in its apical aspect, the ventral suture may occasionally appear quite prominent.

Suture:

*Generally.*—The suture appears as a shallow yet distinct line which extends from the base to the apex and is particularly distinct over the apical shoulder area. Further, the suture blends in with the underlying blush color and a moderate depression occurs on both sides of the apex along the suture line.

Ventral surface:

*Generally.*—Smooth and rounded with some lipping evident on both sides of the fruit.

Stem cavity:

*Generally.*—Moderately deep and narrow. Further, some stem indentation occurs in the vicinity of the shoulders.

*Width.*—Approximately 13 mm.

*Depth.*—Approximately 10 mm.

*Length.*—Approximately 17 mm.

*Shape.*—Slightly oval.

Stem:

*Generally.*—Considered short.

*Caliper.*—Approximately 4 mm.

Apex:

*Shape.*—Rounded and having a low tip. The apex most often appears higher than the apical shoulders and is subtended by depressions disposed on both sides of the apex.

Pistil point:

*Position.*—Apical.

Skin:

*Thickness.*—Considered average.

*Texture.*—Glabrous.

*Tendency to crack.*—Not observed.

*Blush color.*—Red (13. Deep red).

*Ground color.*—Yellow (101. l. g Y).

*Flesh color.*—A clear yellow (83 brill. Y).

*Surface of pit cavity.*—Rough.

*Color of pit well.*—Red, (14. v. deep Red.). The color of the pit well radiates into the flesh a distance of approximately 2–2.5 cm. at commercial maturity. The radiations are red (13. deep Red.).

*Juice production.*—Juicy.

*Flavor.*—A slight peach flavor is detectable at commercial maturity.

*Aroma.*—Slight yet pleasant.

*Texture.*—Firm and crisp at commercial maturity.

*Fibers — numbers.*—Numerous.

*Fibers — texture.*—Average and lightly colored.

*Ripening.*—Even.

*Eating quality.*—Good.

Stone:

*Attachment.*—Clingstone.

*Fibers — numbers.*—Few.

*Fibers — length.*—Moderately long.

*Size — length.*—Approximately 41.5 mm.

*Size — width.*—Approximately 22 mm.

*Size — thickness.*—Approximately 18 mm.

*Form.*—generally — obovate and at times strongly so. Occasionally some oblong shaped stones may be found.

*Apex.*—Shape — Pointed and having a sharp acuminate tip.

*Color.*—Dry — Brown (55 s. Br.). The stone is frequently stained red (17. v. d. Red.).

*Base.*—Shape — Truncate and having a base angle which is variable with both right angles and oblique forms occurring.

*Sides.*—Generally — Equal.

*Hilum.*—Large and well defined.

*Ridges.*—Prominent and high; occasionally irregular pits are also evident.

*Tendency to split.*—Not observed.

Use: Fresh market-type nectarine for use in both local and long distance markets.

Keeping quality: Noteworthy. The subject variety has been placed in cold storage for periods of two to four weeks with no deleterious effects noted.

Resistance to disease: No particular susceptibilities were noted.

Harvesting: The subject variety hangs well on the tree for up to ten days during harvesting with no ill effects noted.

Shipping and handling qualities: Exceptional. The crisp nature of the flesh in combination with the tenacious skin characteristics indicates that the new and novel variety of nectarine tree will have noteworthy shipping and handling characteristics.

Although the new variety of nectarine tree possesses the described characteristics noted above as a result of the growing conditions prevailing near Sultana, Calif., in the Central part of the San Joaquin Valley of Central California, it is to be understood that variations of the usual magnitude and characteristics incident to changes in growing conditions, fertilization, pruning and pest control are to be expected.

Having thus described and illustrated my new variety of nectarine tree, what I claim as new and desire to be secured by Plant Letters Patent is:

1. A new and distinct variety of nectarine tree substantially as illustrated and described and which is somewhat remotely similar to the Sun Grand Nectarine Tree (U.S. Plant Pat. No. 974) with which it is most closely similar but which is distinguished therefrom and characterized principally as to novelty by producing fruit which are mature for commercial harvesting and shipment approximately August 10 through August 20 in the San Joaquin Valley of Central California and which further has noteworthy shipping and handling characteristics.

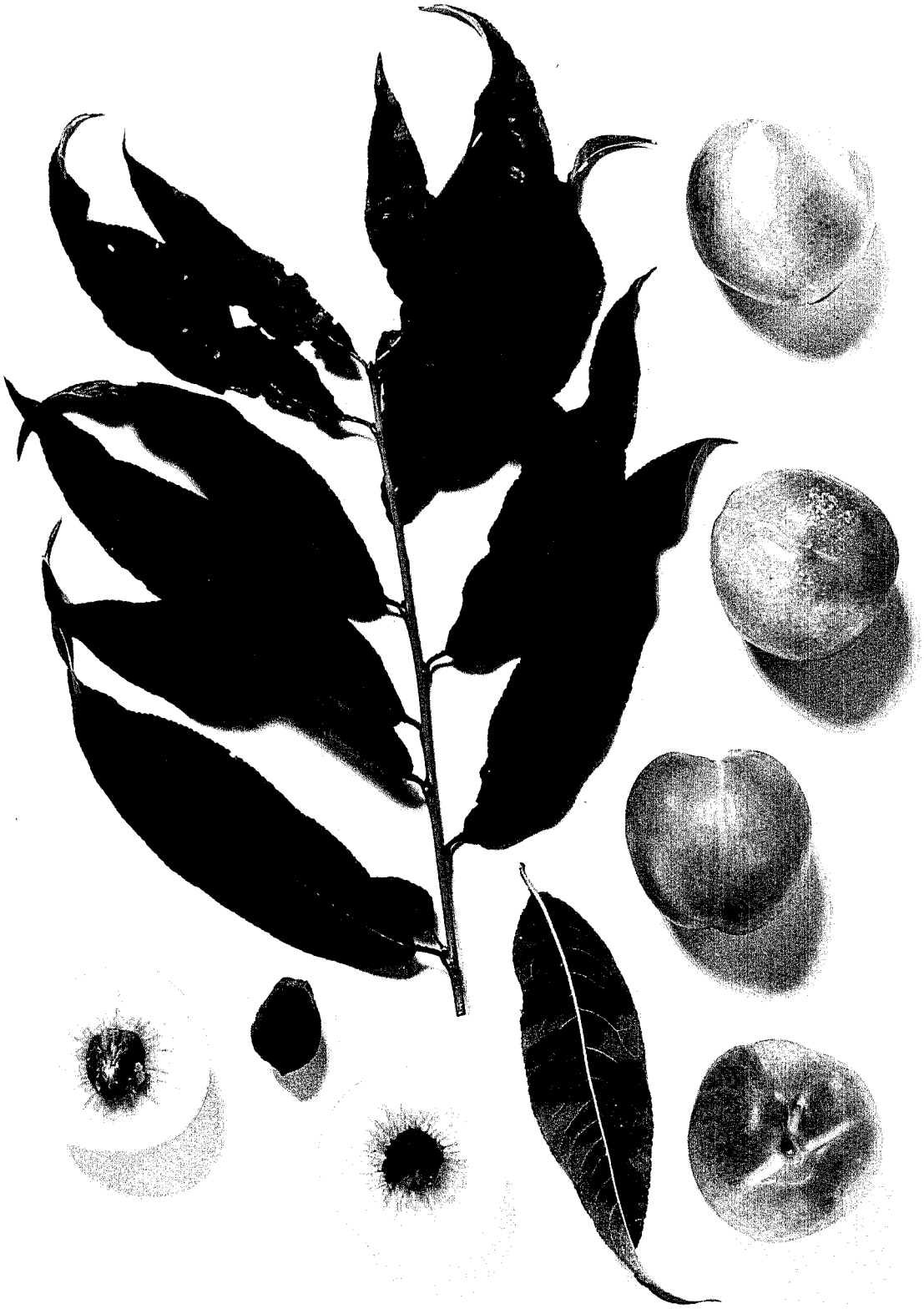

* * * * *